United States Patent [19]

Lötscher

[11] Patent Number: 5,551,437
[45] Date of Patent: Sep. 3, 1996

[54] SENSOR FOR MEASURING BLOOD PRESSURE

[75] Inventor: Bernhard Lötscher, Andelfingen, Switzerland

[73] Assignee: AVL Medical Instruments AG, Schaffhausen, Switzerland

[21] Appl. No.: 256,974

[22] PCT Filed: Dec. 6, 1993

[86] PCT No.: PCT/CH93/00273

§ 371 Date: Aug. 1, 1994

§ 102(e) Date: Aug. 1, 1994

[87] PCT Pub. No.: WO94/13207

PCT Pub. Date: Jun. 23, 1994

[30] Foreign Application Priority Data

Dec. 5, 1992 [CH] Switzerland ............... 3721/92

[51] Int. Cl.⁶ ........................................... A61B 5/02
[52] U.S. Cl. .................................... 128/672; 128/690
[58] Field of Search ................... 125/677, 690, 125/689, 687, 672, 637, 639, 644

[56] References Cited

U.S. PATENT DOCUMENTS

| | | | |
|---|---|---|---|
| 4,030,484 | 6/1977 | Kuska et al. | 128/672 |
| 4,331,154 | 5/1982 | Broadwater et al. | 128/690 |
| 4,409,983 | 10/1983 | Albert | 128/690 |
| 4,443,730 | 4/1984 | Kitamura et al. | 310/330 |
| 4,802,488 | 2/1989 | Eckerle | 128/672 |
| 4,924,871 | 5/1990 | Honeyager | 128/687 |
| 5,005,581 | 4/1991 | Honeyager | 128/672 |
| 5,111,826 | 5/1992 | Nasiff | 128/672 |
| 5,183,050 | 2/1993 | Kawamura | 128/690 |
| 5,243,992 | 9/1993 | Eckerle et al. | 128/690 |
| 5,263,484 | 11/1993 | Martin et al. | 128/672 |
| 5,269,312 | 12/1993 | Kawamura et al. | 128/690 |
| 5,273,046 | 12/1993 | Butterfield et al. | 128/672 |

FOREIGN PATENT DOCUMENTS 2643811  3/1989  France.

*Primary Examiner*—Lee S. Cohen
*Attorney, Agent, or Firm*—Watson Cole Stevens Davis, P.L.L.C.

[57] ABSTRACT

A sensor with a first, second and third force pick-up includes a piece of foil made of piezoelectric material which serves all three pick-ups and carries a number of electrodes. The second and third pick-up are located one on either side of the first pick-up and are characterized by a smaller pick-up surface than the first one. For measuring blood pressure the sensor is pressed against a part of a patient's body such that the first force pick-up, i.e., the one in the middle, is at the shortest possible distance from a large artery. During measurement the absolute values of the changes in the measurement values of the three force pick-ups, which are due to the pulsating blood stream, are added. On the other hand the changes in the measurement values caused by interfering forces will cancel each other out.

13 Claims, 3 Drawing Sheets

5,551,437

SENSOR FOR MEASURING BLOOD PRESSURE

BACKGROUND OF THE INVENTION

1. Field of the Invention

The invention relates to a sensor, a device and a method for measuring blood pressure. This sensor, which is to be applied Lo a part of a live human or, possibly, animal body containing an artery, and the respective device and method are designed to permit non-invasive, long-term measurement of blood pressure in a continuous or at least, quasi-continuous manner, lasting for several hours or days, for instance.

2. The Prior Art

Blood pressure is often measured with instruments that are based on the method of Riva-Rocci and have a hollow, deformable cuff. This is wrapped around a patient's upper arm or some other part of the body, inflated with air and then deflated. As the air is being released, the systolic and the diastolic blood pressure are recorded, based on the Korotkoff sounds generated when the blood flows through an artery, or on some oscillometric measuring method. The Riva-Rocci method is not suitable for any long-term, quasi-continuous kind of measurement, as alternating inflations and deflations of the cuff would be uncomfortable and would probably even damage the patient's health.

Other devices for measuring blood pressure are known, using sensors, for instance, to measure the rate of the blood flow or deformations in the walls of the arteries by means of light or ultrasound. In this context EP-A-0 467 853 is of relevance. Such sensors are comparatively expensive, however, and require most precise positioning.

In U.S. Pat. No. 5,111,826 an instrument for the measurement of blood pressure is described which is provided with a sensor with a piezoelectric force pick-up. For measurement purposes this sensor may be strapped to the patient's finger by means of a fastening device, i.e., a hollow cuff, which is firmly pressed against the finger. The disadvantage of such a sensor is that forces acting upon the force pick-up from outside or as a result of movements of the patient, are likely to produce errors in measurement. Moreover, piezoelectric transducers usually have pyroelectric properties as well, making the sensor sensitive to temperature changes. The cuff, which contains a fluid and subjects the finger to pressure along its entire circumference, may interfere with the patient's blood circulation during long-term measurements, in addition to handicapping him in the use of his hand. Finally, the finger has no large artery that would lend itself to precise measurement.

SUMMARY OF THE INVENTION

It is an object of the invention to propose a sensor, a device and a method for measuring blood pressure without the disadvantages of prior art sensors, devices and methods. Departing from the state of the art known from U.S. Pat. No. 5,111,826 in particular, the invention is aimed at making the measured results as independent as possible from exterior forces, or forces caused by movements of the patient, and temperature changes.

According to the invention a device for measuring blood pressure is provided wherein it includes a sensor having first, second and third force pick-ups, the first force pick-up being located between the second and third force pick-ups; a fastening means for positioning the sensor against a live body such that the first pick-up is pressed near an artery therein; and electronic circuitry for providing measurement variables to measure the blood pressure in the artery.

Further features and advantages of the invention will be understood by reference to the attached drawings taken with the following discussion.

BRIEF DESCRIPTION OF THE DRAWINGS

The invention will be further described with reference to the accompanying drawings, in which.

DETAILED DESCRIPTION OF PREFERRED EMBODIMENTS

Figure 1:
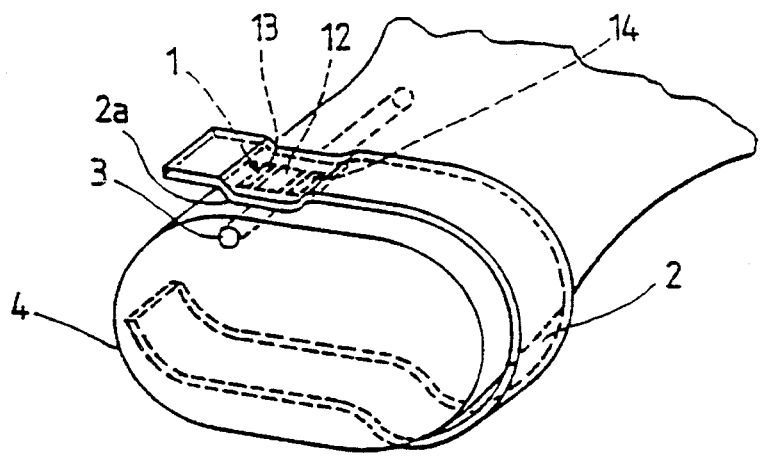
FIG. 1 is an oblique view of the fastening means and the sensor held by them, in a device for measuring blood pressure.

FIG. 1 shows a part 4 of a patient's body, i.e. a region of the lower arm and wrist containing a large artery 3. A device for non-invasive measurement of the blood pressure is provided with sensing means comprising a sensor 1, and fastening means supporting the sensor 1 and pressing it against a part 4 of the patient's body, whose main component is a more or less U-shaped spring clip 2 which may be clipped onto the lower arm from one side so as to be removable, encircling a large part of its circumference. In the area of the surface or skin of part 4 that is closest to the artery 3, this clip 2 is provided with a projection or buckle 2a bulging inwardly, i.e., towards the part 4 of the patient's body, relative to the adjacent parts of the clip, which are either straight or slightly bent. The sensor 1 is removably attached to the at least approximately level surface of the buckle next to the part 4, for example with a piece of double-face adhesive tape, which may be soft and compressible, permitting small deformations and/or movements of the sensor 1. Between the projection or buckle 2a of the clip 2 and the sensor 1 a resilient element made of foam rubber could be placed which would act as a compression spring, permitting the sensor to adapt to the contours of the patient's arm and facilitate bending and stretching.

Figure 2:
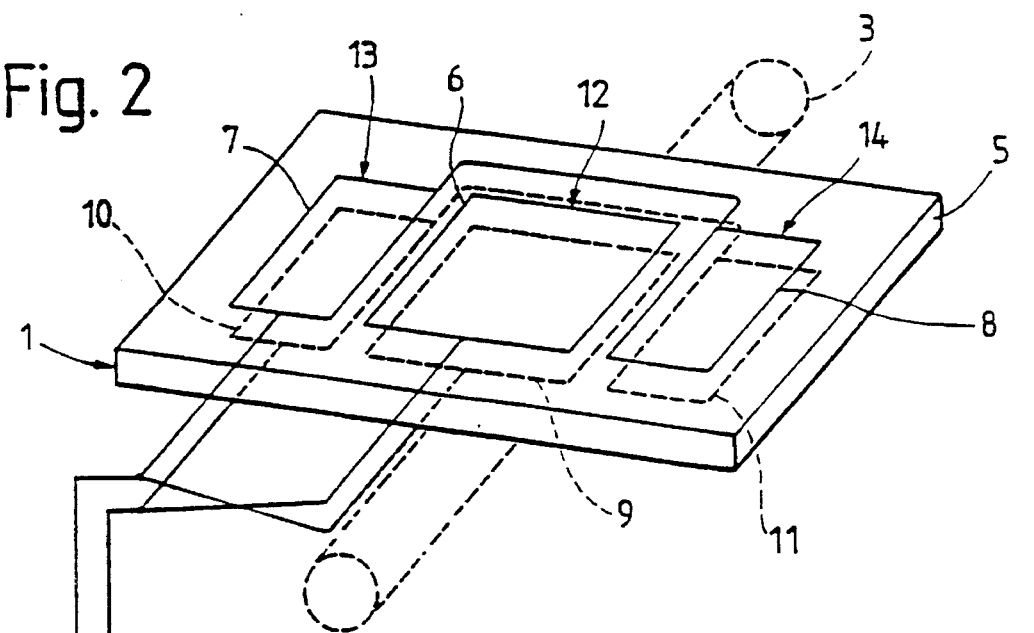
FIG. 2 is a schematical oblique view of the three piezo-electric force pick-ups of the sensor, and a block diagram of the electronic circuitry of the device.

The sensor 1, which is separately shown in FIG. 2, is provided with an element made of piezoelectric material, i.e., a single piece of piezoelectric foil 5. This piece of foil is deformable, in particular bendable, stretchable, and compressible, and is made of plastic, i.e., polyvinylidene difluoride (PVDF). The upper surface of the quadrangular, or rather, rectangular piece of foil 5 (FIGS. 1, 2) is provided with a first or central measuring electrode 6, while a second and third or lateral measuring electrode, 7 and 8, respectively, are located one on either side of the central measuring electrode 6. On the lower surface of the foil 5 three counter-electrodes are located, i.e., a first or central counter-electrode 9, and a second and third or lateral counter-electrode, 10 and 11, respectively. The six measuring and counter-electrodes 6, 7, 8, 9, 10, 11 are of essentially quadrangular or rectangular shape, and form opposing pairs.

The two first or central electrodes 6, 9, together with the part of the foil 5 between them, form a piezoelectric transducer serving as a first or central force pick-up 12. The second and third electrodes 7 and 10, or rather, 8 and 11, which are positioned opposite of each other, together with the parts of the foil 5 between them, form piezoelectric transducers serving as second and third lateral force pick-ups 13 and 14, respectively. In correspondence with the positions of their respective electrodes, the second and third force pick-up 13 and 14 are located one on either side of the first or central pick-up 12. The diverse electrodes consist of thin metal layers remaining after etching away the metal layers originally covering both faces of the foil. The surface of each second and third electrode 7, 10 or 8, 11, is smaller preferably than the surface of each first electrode 6, 9, i.e., approximately or precisely half the size of the surface of each first electrode 6, 9. Correspondingly the pick-up surface of the second and third force pick-up 13 and 14, respectively, which is next to the part 4 of the patient's body while the blood pressure is being measured, is smaller, i.e., approximately or precisely by half, than the pick-up surface of the first force pick-up 12.

The first measuring electrode 6, which is positioned on the upper surface in FIG. 2, is electrically connected with the second and third counter-electrode 10 and 11 located on the lower surface in FIG. 2. The first counter-electrode 9, which is located on the lower surface in FIG. 2, is electrically connected with the second and third measuring electrode 7 and 8 located on the upper surface. The electric conductors necessary for these connections could be wires, or, in parts, tracks on the two opposite faces of the foil 5. The two lateral pick-ups 13, 14 are thus connected electrically parallel to each other and anti-parallel to the first or central force pick-up 12.

The piezoelectric foil 5 may be configured and polarized such that positive forces increasing over time generate a negative charge at the measuring electrodes 6, 7, 8 and a positive charge at the counter-electrodes 9, 10, 11.

The electric charges and/or voltages generated by the first, or second, or third force pick-up will be referred to as first, or second or third measurement variable below. Each of these time-varying measurement variables measures the time-varying force acting on the respective force pick-up, and is at least approximately proportional to this force. If the charge or the potential of a measuring electrode is negative relative to the corresponding counter-electrode, the measurement variable generated by the respective force pick-up is given a negative sign. As the second and third pick-up are connected in parallel, the second and third measurement variable are added algebraically. The resulting total is algebraically subtracted from the first measurement variable.

The device further comprises electronic circuitry 21. This may include a charge amplifier 22 whose inverting input is connected to electrodes 6, 10, 11. The non-inverting input of charge amplifier 22 is connected to electrodes 7, 8, 9. The output of the charge amplifier 22 is connected to an evaluation unit 24 via a manually adjustable resistor serving as an adjusting element 23 for sensitivity adjustment. Together with at least one further adjusting element 25, which may also be configured as a manually adjustable resistor, and with further electronic components, the adjusting element 23 represents a calibration means 26 for setting at least one calibration value and/or calibration parameter, and/or for supplying the evaluation unit 24 with at least one calibration value and/or calibration parameter in the form of an electric analog or digital signal. The evaluation unit 24 may be provided with an analog/digital converter for digitalization of the voltage supplied by the charge amplifier, and a processor for digital processing of the digitalized voltage. The evaluation unit 24 has an output which is connected with a display unit 27. This unit may be designed so as to optionally display either a relative value associated with the systolic or diastolic blood pressure or with a change in blood pressure, or—after previous calibration—the direct or absolute value of the systolic and/or diastolic blood pressure in defined or selectable pressure units, for example by digital display.

For measurement of the blood pressure in a continuous or quasi-continuous process, the sensor 1 is attached to the part 4 of the patient's body with the fastening means comprising the clip 2, such that the central, first force pick-up 12 lies as close as possible to the artery 3 on the surface of part 4 of the patient's body. The two lateral pick-ups 13 and 14 are located slightly off-center, one on either side of the artery 3, at a greater distance from the latter than the first, central force pick-up 12.

The electronic circuitry 21 may be located in a housing which is attached to the patient's body with some sort of fastening elements. If the patient is in a hospital bed, for instance, the circuitry 21 may be positioned at a certain distance from the patient, and may be connected to the sensor 1 by means of disconnectable plug elements.

During measurement the clip 2 will press the sensor 1 against the surface of part 4 with a given pressing force. Part 4 will exert a force on the pick-ups 12, 13, 14 to compensate this pressing force, passing from the artery 3 and part 4 in outward direction. In the static state, i.e., if there were no blood flow through the artery, the outwardly directed force would be distributed at least approximately uniformly over the entire surface of the sensor 1 next to part 4. The static pressure exerted by the part 4 on the close-lying pick-up faces of the force pick-ups 12, 13, 14 would be at least approximately the same for all three of them.

If the heart pumps blood through the artery 3 pulsatingly, and the blood pressure in the section of the artery next to the sensor 1 rises from diastolic to systolic blood pressure during a certain time interval, this rise in pressure will propagate as a pressure pulse towards the surface of the part 4 of the patient's body. As the first, central force pick-up 12 is closer to the artery than the two lateral pick-ups 13, 1.4, the pressure increase at the first pick-up 12 will be larger than at the second and third pick-up 13 and 14. Together with the pressing force exerted on the sensor by the fastening means, the rise in blood pressure will cause an outwardly directed force pulse, which is generated by the pressure pulse, to act on the first force pick-up 12 in addition to the static force. This force pulse acting on the first, central force pick-up 12 has the tendency to push out the entire sensor 1, thus relieving pressure from the second and third force pick-up 13 and 14. A rise in blood pressure will thus lead to a pressure rise at the first, central force pick-up 12, i.e., a change in force, and a reduction in pressure force at the two lateral pick-ups 13, 14. As a consequence, the pressure pulse will produce a change in the first measurement variable represented by an electric signal from the first pick-up 12, and reverse changes in the second and third variable represented by an electric signal from the second and third pick-up 13, 14. The change in the overall electric charge and/or voltage given off by the force pick-ups will be proportional to the sum total of the absolute values of the changes in force measured by the three force pick-ups. The same applies for the changes in force generated by the decline in blood pressure from the systolic to the diastolic value.

The charge amplifier 22 generates an analog electric signal, i.e., an electric voltage. This voltage represents a fourth time-varying measurement variable, which, apart from the sign, is proportional to the value resulting from the described combination of first, second and third variable, i.e., by subtraction of the second and third variable from the first one. The electric voltage representing the fourth measurement variable varies over time in correspondence with the blood pressure. With the use of the evaluation unit 24 the maximum and minimum values of this voltage may be determined and assigned values which are associated with the systolic or diastolic blood pressure. By means of the display unit the values associated with the systolic or diastolic blood pressure may be displayed, either individually or, if so desired, alternatingly or both simultaneously. In this way the value associated with the systolic and/or diastolic blood pressure may be determined and displayed for a prolonged period of time in a continuous or quasi-continuous manner.

Figure 3:
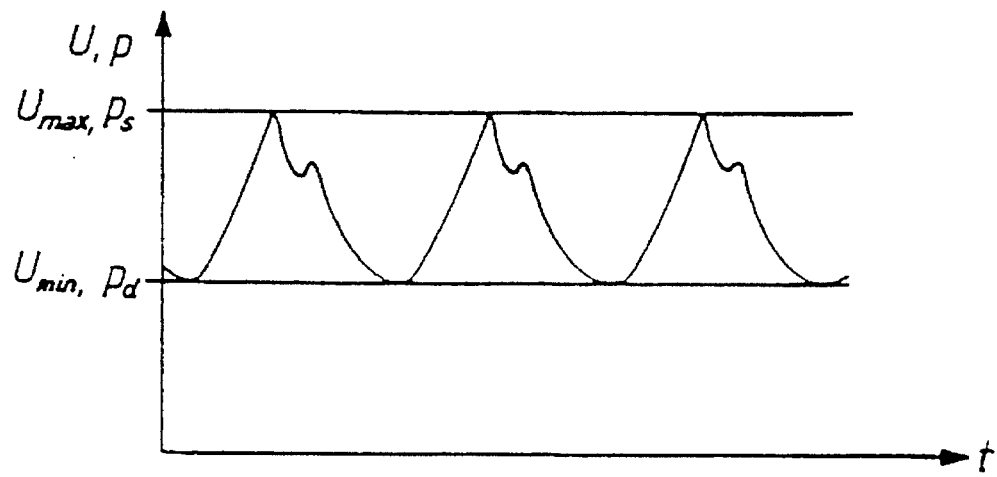
FIG. 3 is a diagram presenting the time curve of a measurement signal and the blood pressure.

With the use of an additional calibration/measuring device based on the Riva-Rocci method, it is possible to perform a calibration measurement on the patient from time to time by temporarily attaching an inflatable cuff, which is part of the device, to one of the patient's arms. By means of the evaluation unit 24 and the calibration means 26 it is possible to set at least one calibration value and/or calibration parameter and/or to feed it to the evaluation unit 24. This is illustrated by the diagram in FIG. 3, where the time t is plotted against the abscissa, and the voltage U entered into the evaluation unit 24, which is proportional to the fourth measurement variable, and the blood pressure p are plotted against the ordinate. The diagram further shows a time curve of the voltage U and the blood pressure p. The voltage U varies between a maximum value $U_{max}$ and a minimum value $U_{min}$. While it is assumed that the voltage U is directly related to the blood pressure, the display unit 27 gives only relative pressure values which do net directly represent a blood pressure value. By means of the calibration/measuring device the systolic blood pressure ps and the diastolic blood pressure pd may be determined and by means of the adjusting elements 23, 25 the voltage U entering the evaluation unit 24 at approximately the same time may be set manually such that the display unit 27 will display the systolic and diastolic pressure in defined or selectable units.

In addition to the pressing force generated by the fastening means and the forces produced by the blood pressure, other exterior forces and/or interfering forces caused by movements of the patient may act on the sensor during operation. If such an interfering force has the same direction at the pick-up faces of all three force pick-ups 12, 13, 14, and is distributed uniformly over the entire surface of foil 5, the pick-up faces of the three force pick-ups are subject to the same force per unit area, and hence to the same pressure in the instance of a pressure force. The changes in the measurement values produced by the three force pick-ups, which are caused by the interfering force, will thus compensate one another to a large extent, preferably even completely. For this reason the interfering force will neither change the overall charge entering the charge amplifier 22 from the connected force pick-ups, nor the corresponding fourth measurement value, so that the blood pressure measurement will remain unaffected. The same applies if the piezoelectric force pick-ups 12, 13, 14 generate charges or voltages as a result of a temperature change, thereby changing the first three measurement values.

Figure 4:
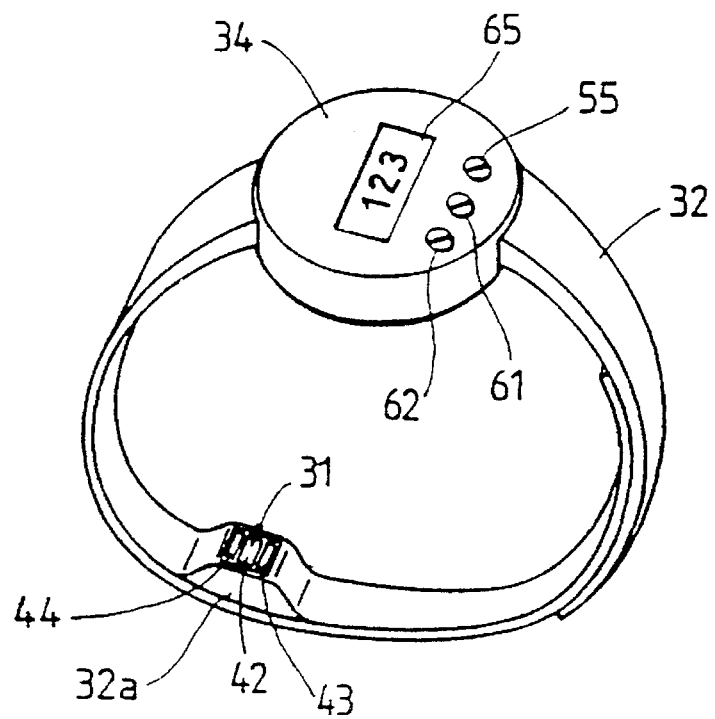
FIG. 4 is an oblique view of another device for measuring blood pressure, with a strap to be tied to an arm, which supports a sensor and a housing with electronic circuitry and, FIG. 5 is a block diagram of the force pick-ups and the electronic circuitry of the device of FIG. 4.
Figure 5:
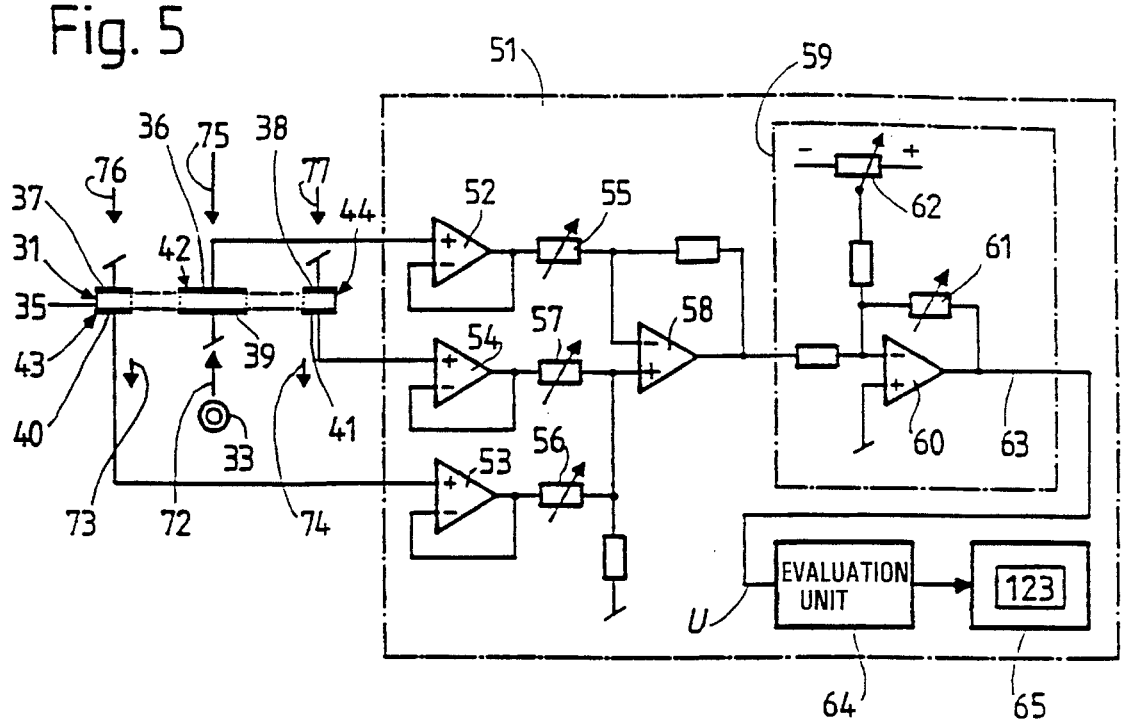

FIGS. 4 and 5 present the outer appearance and a block diagram of another device used for measuring blood pressure. This device comprises a sensor 31 and fastening means including a strap 32. The latter may consist of two separate parts whose one ends are attached to a housing 34 and whose other ends are held together so as to be separable, for example by a touch-and-close tape or some other fastener. The strap 32 is designed so as to encircle the lower arm of the patient near the wrist, enabling the patient to wear the blood measuring device like a watch. The strap 32 has a projection or buckle 32a. When the strap 32 is wrapped around the arm the projection or buckle 32a bulges inwardly, pressing against the arm. The sensor 31 is fastened to the surface on the projection or buckle 32a lying next to the arm during use. The projection or buckle 32a is made, at least partly, of material acting as a compression spring, for example, foam rubber. The projection or buckle 32a enables the sensor 31 to be pressed against the arm with a given pressure force without necessitating close contact between the entire strap and the arm, and without requiring the strap 32 to be unduly tight, so that the arm's blood circulation will be left unimpeded. The sensor 31 and/or at least part of the projection or buckle 32a preferably is connected to the strap 32 so as to be detachable, in order to permit easy replacement of the sensor.

The sensor 31 is provided with a single piece of piezoelectric foil 35, as is shown in FIG. 5. The center part of the foil 35, together with a measuring electrode 36 and a counter-electrode 39 constitutes a first, central force pick-up 42. The two lateral parts of the foil 35, together with a second and third measuring electrode 37 and 38, respectively, and a second and third counter-electrode 40 and 41, respectively, constitute a second and third, lateral force pick-up 43 and 44, respectively. The sensor 32 may be tied to the arm by means of the strap 32 such that it lies close to it in the vicinity of a large artery 33, as indicated in FIG. 5.

FIG. 5 also shows electronic circuitry 51. It is located in the housing 34 and comprises three amplifiers forming a fist voltage follower 52, a second voltage follower 53, and a third voltage Follower 54 The non-inverting input of the first voltage Follower 52 is connected to the measuring electrode 36 of the first force pick-up 42. The non-inverting inputs of the second and third voltage follower 53 and 54, respectively, are connected to the counter-electrode 40 and 41, respectively, of the second and third force pick-up 43 and 44, respectively. The other electrodes 37, 38, 39 are connected to circuit mass.

The output of the first voltage follower 52 is connected to the inverting input of a differential amplifier 58 via a manually adjustable resistor serving as an adjusting element 55. The outputs of the other two voltage followers 53, 54 are connected to the non-inverting input of the differential amplifier 58 via manually adjustable resistors serving as adjusting elements 56, 57. The output of the differential amplifier 58 is connected to the input of calibration means 59 comprising an amplifier 60 and two manually adjustable adjusting elements 61 and 62, one of which acts as an inverse feedback resistor and the other one as a voltage divider resistor. Via an evaluation unit 64, which is provided with an analog/digital converter and, possibly, a processor, the output 63 off the amplifier 60 is connected to a display unit 65, which is configured as a digital display, for example.

During operation of the device shown in FIGS. 4 and 5 the Forces picked up by the three force pick-ups 42, 43, 44 are converted by them into electric measurement signals, i.e., charges and/or voltages. The electric measurement signals generated by the first, second, and third force pick-up are separately processed by the three voltage followers 52, 53, 54. The electric voltages supplied to the differential amplifier 58 by the three adjusting elements 55, 56, 57 represent the first, second and third measurement variable. The changes over time of the three measurement variables are proportional to those of the signals generated by the corresponding force pick-up, the proportionality factors being separately adjustable by means of the adjusting elements 55, 56, 57. The differential amplifier 58 will subtract the second and third measurement variable from the first one. Due to the adjusting elements 55, 56, 57 the proportionality factors may be adjusted to individual properties of the patient's arm, for instance, position and shape of the artery 33, and the tissue surrounding it, such that changes in the measurement signals which are due to interfering forces at the force pick-ups, are largely or even totally compensated.

The device shown in FIGS. 4 and 5 may be calibrated at the beginning of a continuous measurement of blood pressure. If the measurement takes a long time, new calibrations may be performed from time to time. For the purpose of calibration, the systolic and diastolic blood pressure may be determined with an additional calibration/measuring unit, as described for the device shown in FIGS. 1 and 2, and the voltage U supplied to the evaluation unit 64 may be adjusted in correspondence with the values measured by the calibration/measuring device such that the display unit 65 will directly display the systolic and/or diastolic blood pressure. By means of the adjusting element 61, i.e., the inverse feedback resistor, the difference between the maximum value $U_{max}$ and the minimum value $U_{min}$ of the voltage U supplied to the evaluation unit 64 can be adjusted such that the difference between the two voltages $U_{max}$ and $U_{min}$ of the displayed pressure values equals the difference between the values obtained by means of the calibration/measuring device for the systolic and diastolic blood pressure, $p_s$ and $p_d$. With the use of the adjusting element 62 it will then be possible to adjust the zero point in such a way that the pressure values indicated by the display unit 65 correspond to the systolic and diastolic blood pressure.

In FIG. 5 the pulse-induced change in force 72 acting on the first, central force pick-up 42 upon a rise of arterial blood pressure is indicated by an arrow. Other arrows represent the subsequent force changes 73, 74 relieving the lateral force pick-ups 43, 44. During measurement the absolute values of the Force changes caused by the pulsating blood flow are combined according to the settings of the adjusting elements 55, 56, 57, i.e., their weighted sum is formed.

FIG. 5 also shows interfering forces 75, 76, 77 acting on the three force pick-ups from outside. If these forces are generated by a pressure which is the same for all pick-ups, the interfering force 75 acting upon the central force pick-up 42 is greater—on account of the larger pick-up surface of this pick-up—than the interfering forces 76, 77 acting upon the two lateral force pick-ups. During the combination of the first, second, and third measurement variable taking place at the differential amplifier 58, the interfering forces are compensated.

The devices may be modified in various respects. The three counter-electrodes of sensors 1 and 31 may be replaced by a single connected counter-electrode, for example, which serves all three force pick-ups of the sensor. The sensors 1 and 31 may be shielded by metal layers enclosing their electrodes. Moreover, the surfaces of the sensors carrying the electrodes may be coated with two electrically-insulating layers each, between which is provided an electrically conductive shielding layer.

The calibration means 26, 59 may be configured such that they can be electrically connected to the calibration/measuring device. The latter may have a processor in order to supply the calibration means 26, 59 with calibration values and to automatically calibrate the electronic circuitry 21, 51.

It is of course possible to combine properties of the two devices illustrated by the drawings.

The parts of the piezoelectric foil belonging to the two lateral force pick-ups may be inversely polarized relative to the part of the foil of the first, central force pick-up. Instead, the three force pick-ups may each be provided with a separate piezoelectric element made of plastic foil or some ceramic or crystalline material, and the elements of the two lateral force pick-ups may be inverse relative to the element of the central force pick-up. The three separate force pick-ups may be attached to an element which connects them mechanically. In these two variants the foils or other piezoelectric elements are configured such that changes of force acting in the same direction will produce electric charges and voltages at the electrodes positioned on the same side or surface, whose sign at the first, central force pick-up is opposite to the signs at the two lateral force pick-ups.

Each of the devices for measuring blood pressure may further be provided with a second sensor of the same configuration as the one described. The two sensors may be positioned on the patient's arm in different places along the artery 3 or 33. The electronic circuitry may be designed no calculate the pulse wave velocity from the shift in time between the time-varying measurement values measured by the two sensors, and to utilize it in turn for determination of the blood pressure. This may be achieved with methods as described in the previously cited EP-A-0 467 853. In this context specific reference is made to the contents of EP-A-0 467 853.

I claim:

1. A combination of a sensor for measuring blood pressure and a fastening means for positioning the sensor against a live body, said sensor comprising first, second and third force pick-up means for detecting pulses of blood passing through an artery in a live body, said first force pick-up means being located between said second and third force pick-up means, each of said first, second and third force pick-up means defining a surface which can be positioned close to a live body containing an artery, the surfaces of said second and third force pick-up means being smaller than the surface of said first force pick-up means, and said fastening means positioning the sensor against a live body so that said first force pick-up means is pressed against a part of the live body containing an artery therein.

2. A sensor as in claim 1, wherein the first, second and third force pick-up means (14, 44) are configured as piezoelectric transducers.

3. A sensor as in claim 1, wherein the first, second and third force pick-up means are provided with one common piece of flexible foil which is made of piezoelectric material and carries a number of electrodes.

4. A sensor as in claim 1, wherein the fastening means are provided with at least one spring component elastically pressing the first, second and third force pick-up means against the live body.

5. A device for measuring blood pressure with a sensor comprising first, second and third force pick-ups, said first force pick-up being located between said second and third force pick-ups, and a fastening means for pressing said first force pick-up against a part of a live body containing an artery, said device including electronic circuitry, wherein the sensor and the circuitry provide a first measurement variable, and a second measurement variable, and a third measurement variable measuring at least one of the force and the change of force obtained from the first, second, and third force pick-ups, and to combine the three measurement variables, wherein the second and third force pick-ups are connected electrically parallel to each other and antiparallel to the first force pick-up.

6. A device as in claim 5, including a housing containing at least part of the electronic circuitry, said housing being supported by the fastening means.

7. A device for measuring blood pressure with a sensor comprising first, second and third force pick-ups, said first force pick-up being located between said second and third force pick-ups, a fastening means for pressing said first force pick-up against a part of a live body containing an artery, and electronic circuitry, wherein the sensor and the circuitry provide a first measurement variable, and a second measurement variable, and a third measurement variable measuring at least one of the force and the change of force obtained from the first, second, and third force pick-ups, and to combine the three measurement variables, wherein the electronic circuitry is provided with at least one manually adjustable adjusting element in order to adjustably combine at least one of the first, second and third measurement variables with an electric signal generated by the respective force pick-up.

8. A device as in claim 5, wherein the electronic circuitry is provided with calibration means for setting and/or entering at least one calibration value, and/or can be connected thereto, permitting determination of the systolic and/or diastolic blood pressure in at least quasi-continuous fashion after at least one calibration value has been set and/or entered, this value having been obtained by a measurement on the body with a calibration/measuring device.

9. A device as in claim 7, wherein the circuitry comprises a subtraction unit combining the three measurement variables of said force pick-ups in such a way that the absolute values of the changes in the second and third measurement variable are subtracted from the absolute value of the change in the first measurement variable if these changes are produced by an increase in the pressure forces acting on the three force pick-ups.

10. A device as in claim 7, wherein the circuitry comprises a subtraction unit to subtract the second measurement variable and the third measurement variable from the first measurement variable, thus forming a fourth measurement variable as a measure for the blood pressure.

11. A device as in claim 7, including a housing containing at least part of the electronic circuitry, said housing being supported by the fastening means.

12. A device as in claim 7, wherein the electronic circuitry is provided with calibration means for setting and/or entering at least one calibration value, and/or can be connected thereto, permitting determination of the systolic and/or diastolic blood pressure in at least quasi-continuous fashion after at least one calibration value has been set and/or entered, this value having been obtained by a measurement on the body with a calibration/measuring device.

13. A method for measuring blood pressure utilizing a sensor comprising first, second and third force pickups, said first force pick-up being located between said second and third force pick-ups, and a fastening means for pressing said first force pick-up against a part of a live body containing an artery, each of said first, second and third force pick-ups having a pick-up surface, wherein the pick-up surface of the second and third force pick-ups is smaller than the pick-up surface of the first force pick-up, wherein said method comprises the steps of positioning the sensor on a live body in such a way that the first force pick-up is closer to an artery than the second and third force pick-ups, detecting blood pulses passing through said artery with said first, second and third force pick-ups, and determining the blood pressure in said artery from said detected blood pulses.

* * * * *